United States Patent [19]

Bergeron, Jr.

[11] Patent Number: 6,160,022

[45] Date of Patent: Dec. 12, 2000

[54] CHEMICAL RESECTION OF PANCREAS

[75] Inventor: Raymond J. Bergeron, Jr., Gainesville, Fla.

[73] Assignee: University of Florida, Gainesville, Fla.

[21] Appl. No.: 09/357,165

[22] Filed: Jul. 19, 1999

[51] Int. Cl.$^7$ .......................... A61K 31/13; A01N 35/00
[52] U.S. Cl. ............................................. 514/674
[58] Field of Search ............................................. 514/674

[56] References Cited

U.S. PATENT DOCUMENTS 5,434,145  7/1995  Edwards et al. ........................ 514/108

*Primary Examiner*—Marianne M. Cintins
*Assistant Examiner*—Donna Jagoe
*Attorney, Agent, or Firm*—Miles & Stockbridge; Dennis P. Clarke

[57] ABSTRACT

A method of chemically resecting the exocrine portion of the pancreas of a patient in need thereof comprising administering to the patient an amount of a hydroxy polyamine or a salt thereof with a pharmaceutically acceptable acid sufficient to resect the exocrine portion of the pancreas thereof, but insufficient to substantially alter the endocrine portion thereof. The hydroxy polyamine has a structure according to the formula:

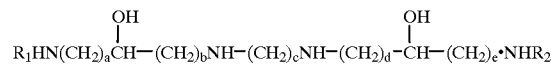

wherein: $R_1$ and $R_2$ may be the same or different and are alkyl
  having 1 to 6 carbon atoms or aryl or aralkyl having up to 12 carbon atoms;
  a, b, d and e may be the same or different and are integers from 1 to 4; and
  c is an integer from 2 to 6.

A pharmaceutical composition in unit dosage form comprising the hydroxy polyamine or a salt thereof with a pharmaceutically acceptable acid for use in the method of the invention is also disclosed.

2 Claims, 1 Drawing Sheet

CHEMICAL RESECTION OF PANCREAS

BACKGROUND OF THE INVENTION

1. Field of the Invention

The invention relates to novel chemical compositions and methods for the resection of the exocrine portion of the pancreas.

2. Discussion of the Prior Art

Pancreatic tumors result in the death of more than 95% of afflicted patients [Isselbacher et al, (ed.) *Harrison's Principles of Internal Medicine,* 13th edition, pages 1532–1534 (1994)]. More than 26,000 people die each year in our country from pancreatic adenocarcinoma. It is the fourth most common cause of cancer death in men and the fifth most common for women. Overall, it is the fourth most common carcinoma after those of the lung, colon and breast. The incidence of this disease is linear with age to sixty, but its occurrence increases markedly in the seventh or eighth decade of life. There are several different histologies associated with cancer of the pancreas, including small cell cancer, cystadenocarcinoma, islet cell tumors, lymphoma and carcinoid; however, 75–80% of the cases involve adenocarcinomas of ductal origin.

Pancreatic tumors occur twice as frequently in the pancreatic head (60% of cases) as in the body (15–20%) or tail (about 5%) of the gland [Cotran et al, (ed.) *Rubbins Pathologic Basis of Disease,* 4th edition, pages 988–992 (1989)]. Currently, complete surgical resection of pancreatic tumors offers the only effective treatment of this disease. Surgical resection, however, is limited, for all practical purposes, to those individuals having tumors in the pancreatic head and in whom jaundice was the initial symptom. Even with the operation, the five-year survival rate for these patients is only 5% [Isselbacher et al, supra]. Only 15–25% of tumors are resectable at the time of diagnosis and only 10–20% of patients resected will survive more than two years. With these less than satisfactory surgical results, present day therapy has evolved in two directions: palliation of symptoms and aggressive multimodality treatment regimes which combine surgery with chemotherapy and radiation treatment.

Located in the upper abdomen in the retroperitoneum, the pancreas is associated intimately with many major structures, including the portal vein, stomach, duodenum, common bile duct and the superior mesenteric artery. As the tumor grows, the patient's symptoms result from tumor infiltration of surrounding structure causing pain, nausea, vomiting, weight loss and jaundice. The latter condition presents symptoms in no more than one-half of the patients. Once tumor infiltration occurs, other structures such as the portal vein become affected and this precludes curative resecting of the pancreas.

Effective treatment of pancreatic cancer must achieve two difficult goals: control of the primary tumor mass, both initially and subsequently, and treatment of the metastatic tumor cells. As a result of its insidious onset, the diagnosis of pancreatic cancer is delayed frequently for several months. This delay has profound implications since metastatic spread to the liver or lymph nodes has been observed at a time of diagnosis in 60% of patients and this factor diminishes the prospect for long-term survival. Also, there are no known specific markers of carcinoma of the pancreas and it is asymptomatic in its early stage.

Palliative therapy has become a major thrust of current treatment. Initial relief of symptoms has relied on surgery with surgical by-pass of gastric outlet obstruction and operative by-pass of biliary obstruction. Subsequent symptomatic treatment has centered around endoscopic placement of biliary stents to by-pass tumors blocking the biliary tract and/or percutaneous placement of by-pass conduits.

Aggressive multimodality therapy combining chemotherapy and radiation therapy has been the response of choice when surgery alone was not effective. Radiation has been the cornerstone of therapy for non-resectable cancer of the pancreas and 5-fluorouracil (5-FU) chemotherapy has been an important adduct to radiation treatment in these patients. However, despite these valiant efforts, few patients survive five years.

Effective radiotherapy needs to maximize exposure of the affected tissues while sparing normal surrounding tissues. Interstitial therapy, where needles containing a radioactive source are embedded in the tumor, has become a valuable new approach. In this way, large doses of irradiation can be delivered locally while sparing the surrounding normal structures. Intraoperative radiotherapy, where the beam is placed directly onto the tumor during surgery while normal structures are moved safely away from the beam, is another specialized radiation technique. Again, this achieves effective irradiation of the tumor while limiting exposure to surrounding structures. However, despite the obvious advantage of approaches predicated upon local control of the irradiation, patient survival is not significantly improved.

The foundation of chemotherapy for carcinoma of the pancreas has employed 5-FU. Here, too, the prognosis is bleak: no better than 10–15% of patients treated with 5-FU will experience a significant reduction in tumor size; overall survival rates are not improved. The addition of other chemotherapeutic agents such as cis-platin or adriamycin has not dramatically improved disease management. For this reason, attempts to augment the intrinsic activity of 5-FU have been undertaken. In one approach, 5-FU is converted to 4-fluorode-oxyuridine monophosphate (FdUMP) which binds covalently to thymidylate synthase. This competitive inhibitor disrupts DNA replication by curtailing deoxyuridine monophosphate anabolism to deoxythymidine.

New experimental efforts in treating pancreatic cancer have been initiated; however, their limited success emphasizes the need for radically new approaches in the management of this devastating disease.

There exist, of course, other pancreatic pathologies which require intervention for their relief, e.g., pancreatitis.

It is an object of the present invention to provide novel compositions and methods for the chemical resection of all or a portion of the pancreas in human or non-human mammals.

SUMMARY OF THE INVENTION

The above and other objects are realized by the present invention, one embodiment of which relates to a method of chemically resecting the exocrine portion of the pancreas of a human or non-human mammal in need thereof comprising administering to said mammal an amount of a hydroxy polyamine or a salt thereof with a pharmaceutically acceptable acid sufficient to resect the exocrine portion of the pancreas thereof, but insufficient to substantially alter the endocrine portion thereof, said hydroxy polyamine having a structure according to the formula:

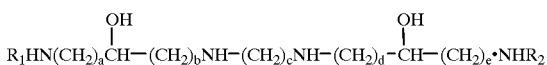

wherein: $R_1$ and $R_2$ may be the same or different and are alkyl
having 1 to 6 carbon atoms or aryl or aralkyl having up to 12 carbon atoms;
a, b, d and e may be the same or different and are integers from 1 to 4; and
c is an integer from 2 to 6.

Another embodiment of the invention relates to a pharmaceutical composition in unit dosage form comprising (1) an amount of a hydroxy polyamine or a salt thereof with a pharmaceutically acceptable acid sufficient, when administered to a human or non-human mammal in need thereof, to resect the exocrine portion of the pancreas thereof, but insufficient to substantially alter the endocrine portion thereof, said hydroxy polyamine having a structure according to the formula:

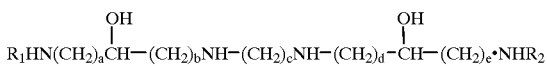

wherein: $R_1$ and $R_2$ may be the same or different and are alkyl having 1 to 6 carbon atoms or aryl or aralkyl having up to 12 carbon atoms;
a, b, d and e may be the same or different and are integers from 1 to 4; and
c is an integer from 2 to 6; and
(2) a pharmaceutically acceptable carrier therefor.

DETAILED DESCRIPTION OF THE INVENTION

Figure 1:
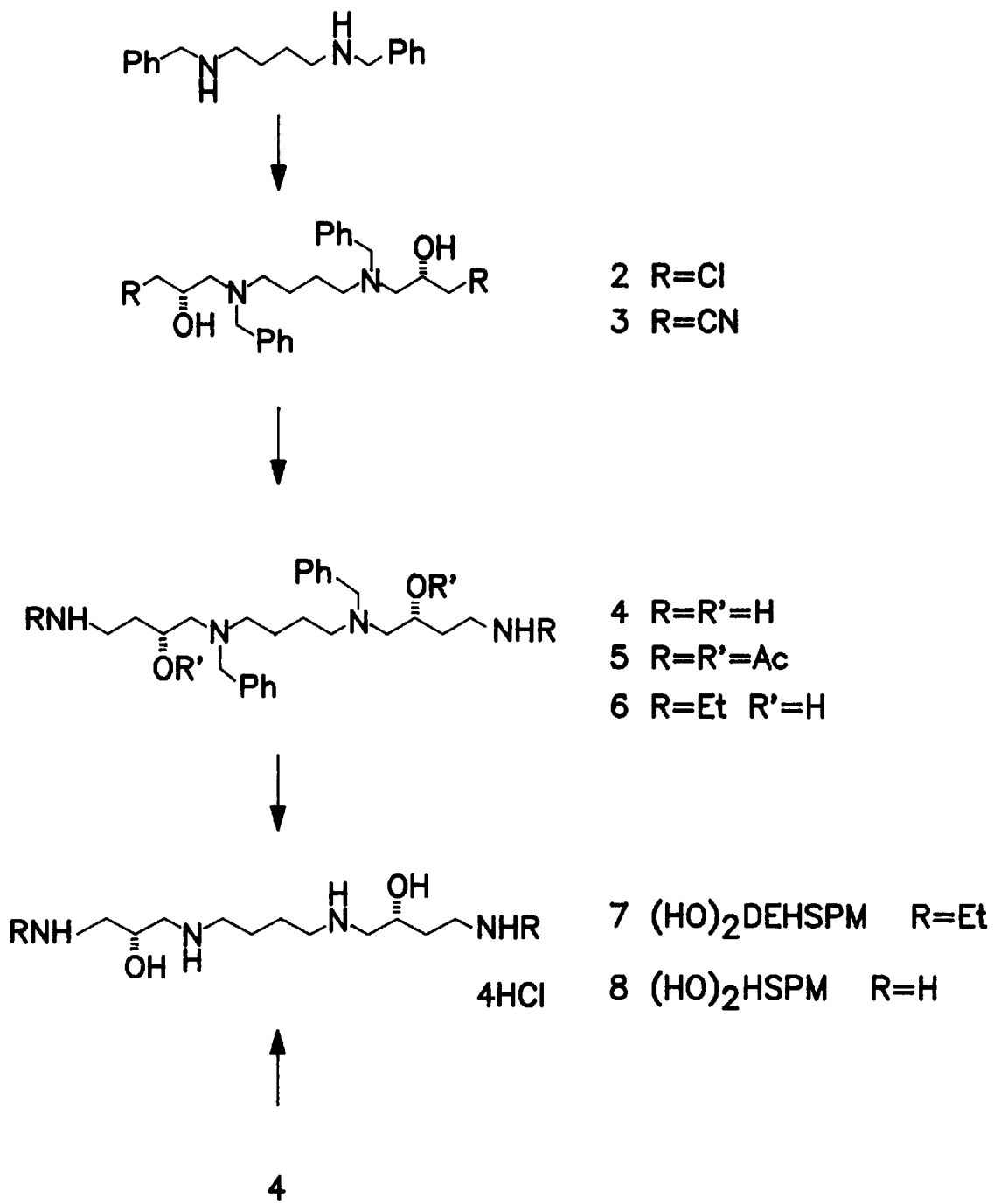
FIG. 1 is a schematic diagram of a reaction scheme for preparing the hydroxy polyamines of the invention.

The present invention is predicated on the discovery that the administration of hydroxy polyamines of the above formula or their salts, complexes or derivatives to mammals in certain doses over time results in the resection of the exocrine portion of the pancreas.

The mechanism by which these hydroxy polyamines and their derivatives resect only the exocrine portion of the pancreas is unknown. It is noted, however, that the termini of these hydroxy polyamines are very similar in structure to the non-carboxylic terminus of hypusine which has the structure:

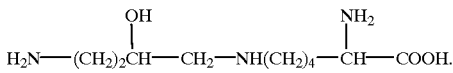

It is theorized that the mechanism of exocrine pancreatic resection associated with the present invention relates to the ability of the hydroxy polyamines of the invention to mimic hypusine in the exocrine cells of the pancreas, thereby inhibiting the function and/or synthesis of hypusine which is integral to protein synthesis and thus to the viability of the exocrine portion of the pancreas.

It is not yet understood why the hydroxy polyamines function only to resect the exocrine portion of the pancreas while having substantially no effect in the endocrine portion thereof.

Referring to the above structural formula, $R_1$ and $R_2$ are preferably alkyl of 1–6 carbon atoms, e.g., methyl, ethyl, propyl, butyl or aralkyl groups such as benzyl and the like.

Referring to the above structural formula, a and e are preferably 2; b and d are preferably 1; and c is preferably 4.

Also referring to the above structural formula, the stereochemistry at the two hydroxyl groups are preferably in the (R,R) or (S,S) configurations, but the (S,R) and (R,S) isomers may also be useful.

The hydroxy polyamines utilized in the practice of the invention may be prepared according to the methods described in U.S. patent application Serial No. 08/595,877 filed Feb. 6, 1996, now U.S. Pat. No. 5,962,533 the entire contents and disclosure of which are incorporated herein by reference.

Briefly, the hydroxy polyamines are prepared according to the reaction scheme set forth in FIG. 1 for the synthesis of $3(R),12(R)$-dihydroxy-$N^1,N^{14}$-diethylhomospermine $[(HO)_2$-DEHSPM] (7) and $4(R),13(R)$-dihydroxyhomospermine $[(HO)_2$HSPM] (8).

The synthesis of polyamines $(HO)_2$DEHSPM (7) and $(HO)_2$HSPM (8), which contain chiral alcohols on the outer methylene chains, was accomplished by methodology used to prepare hypusine [Bergeron et al, *J. Org. Chem.*, Vol. 58, pages 6804–6806 (1993)]. N,N'-Dibenzylputrescine [Samejima et al, *Chem. Pharm. Bull.*, Vol. 32, pages 3428–3435 (1984)] added regiospecifically to (S)-(+)-epichlorohydrin (2 equiv) to form (S,S)-bis-chlorohydrin 2. Treatment of 2 with KCN in the presence of 18-crown-6 afforded dinitrile 3 in which the alcohols are now in the (R)-configuration (i.e., diethyl). The cyano groups of 3 were hydrogenated with Raney nickel in methanolic ammonia, resulting in primary α, ω-diamine 4. Hydrogenolysis of the N-benzyl protecting groups of 4 under mild conditions (1 atm, 10% Pd-C, ethanol, 4 equiv HCl) furnished 3(R) ,12 (R)-dihydroxyhomospermine tetrahydrochloride (8). Compound 4 was also exhaustively acylated with acetic anhydride in methylene chloride. Exposure of the resulting 5 to LiAlH$_4$ in THF simultaneously reduced the acetamides to ethyl amines and unmasked the secondary carbinols. Catalytic removal of the benzyl protecting groups of 6 as above afforded terminally diethylated homospermine (R,R) diol 7 as its tetrahydrochloride salt. Substitution of (S)-(+)-epichlorohydrin with (R)-(−)-epichlorohydrin or the racemate would yield the corresponding isomers.

Polyamines of the present invention can possess one or more asymmetric carbon atoms and are thus capable of existing in the form of optical isomers, as well as in the form of racemic or non-racemic mixtures thereof. The preferable isomers are the (R,R) and (S,S) isomers, but also useful are the (R,S) and (S,R) isomers. The optical isomers can be obtained by stereospecific reactions utilizing optically active starting materials or by stereospecific resolution of the racemic mixtures according to processes known to those skilled in the art, for example, by formation of diastereoisomeric salts by treatment with an optically active acid or base. Examples of appropriate acids are tartaric, diacetyltartaric, dibenzoyltartaric, ditoluoyltartaric and camphorsulfonic acid and the like, followed by separation of the mixture of diastereoisomers by crystallization, then release of the optically active bases from these salts. Another example of a process for separation of optical isomers involves the use of a chiral chromatography column optimally chosen to maximize the separation of the enantiomers.

The following examples exemplify the above-described method for preparing 4(R),13(R)-dihydroxyhomospermine $[(HO)_2$-HSPM].

EXAMPLE 1

4,9-Dibenzyl-1,12-dichloro-2(S), 11(S)-dihydroxy-4,9-diazadodecane (2).

$MgSO_4$ (5 g) was added to a solution of 1 (5.45 g, 20.3 mmol) and (S)-(+)-epichlorohydrin (4.13 g, 44.7 mmol) in distilled methanol (120 ml). The reaction mixture was stirred at room temperature for 2 days until completion of the reaction as monitored by TLC. The solid was filtered and the filtrate was concentrated in vacuo to leave an oil. Flash chromatography with 80/15/5 hexane/EtOA/EtOH afforded 6.23 g (68%) of 2 as an oil: NMR δ1.40 (m, 4 H)f 2.50 (m, 8 H), 3.50 (m, 4 H), 3.56 (dd, 4 H, J=25.6 and 1.2), 3.80 (m, 2 H), 7.27 (m, 10 H). Anal. calcd. for $C_{24}H_{34}Cl_2N_2O_2$: C 63.57, H 7.56, N 6.18. Found: C 63.41, H 7.61, N 6.23.

EXAMPLE 2

4.9-Dibenzyl-1,12-dicyano-(R), 11(R)-dihydroxy-4,9-diazadodecane (3).

A mixture of 2 (2.91 g, 6.4 mmol), KCN (4.18 g, 64 mmol) and 18-crown-6 (0.17 g, 0.64 mmol) in dry acetonitrile (80 ml) was heated at 60° C. for 2 days. The solid was filtered and solvent was removed by rotary evaporation. The residue was purified using flash column chromatography with 60/35/5 hexane/EtOAc/EtOH to afford a solid which was recrystallized from 30/70 $CH_2Cl_2$/hexane to furnish 1.8 g (65%) of 3 as a white solid: mp 85° C.; NMR δ1.46 (m, 4 H), 2.48 (m, 12 H), 3.60 (dd, 4 H, J=24.2 and 4.5), 3.73 (m, 2 H), 7.29 (m, 10 H). Anal. calcd. for $C_{26}H_{34}N_4O_2$: C 71.86, H 7.89, N 12.89. Found: C 71.78, H 7.95, N 12.80.

EXAMPLE 3

$N^5,N^{10}$-Dibenzyl-3(R),12(R)-dihydroxyhomospermine (4).

W-2 grade Raney nickel (0.7 g) was added to a solution of 3 (1.42 g, 3.04 mmol) in methanol (100 ml) in a 500 ml Parr bottle and a slow stream of $NH_3$ was bubbled through the mixture for 20 minutes at 0° C. Hydrogenation was carried out with shaking at 50 psi for 7 hours. The suspension was filtered through Celite, and the solvents were evaporated in vacuo to afford 1.12 g (86%) of 4 as an oil: NMR δ1.41 (m, 4 H), 2.42 (m, 8 H), 2.82 (m, 8 H), 3.55 (d, 4 H, J=2.6), 3.71 (m, 2 H), 7.52 (m, 10 H). HRMS calcd. for $C_{26}H_{43}N_4O_2$:443.3386 (M+1). Found: 443.3383 (M +1).

EXAMPLE 4

3(R), 12(R)-Diacetoxy-$N^1$, $N^{14}$-diacetyl-$N^5$, $N^{10}$-dibenzyl-homospermine (5).

A solution of 4 (2.4 g, 5.42 mmol) in $CH_2Cl_2$ (100 ml) was treated with acetic anhydride (10 ml) at room temperature for 3 hours. The volatiles were evaporated in vacuo and the concentrate was purified by flash chromatography with 65/25/15 hexane/EtOAc/EtOH to give 2.39 g (73%) of 5 as an oil: NMR δ1.44 (m, 4 H), 1.96 (m, 3 H), 1.98 (,m, 4 H), 2.07 (s, 3 H), 2.46 (m, 8 H), 2.57 (m, 2 H), 3.02 (m, 2 H), 3.42 (m, 2 H), 3,59 (m, 4 H), 7.28 (m, 10 H). Anal. calcd. for $C_{34}H_{50}N_4O_6$: C 66.86, H 8.25, N 9.17. Found: C 66.81, H 8.22, N 9.16.

EXAMPLE 5

$N^5,N^{10}$-Dibenzyl-$N^1$, $N^{14}$-diethyl-3 (R) 12 (R)-dihydroxy-homosermine (6).

$LiAlH_4$ (1 m in THF, 15 ml, 15 mmol) was added to a solution of 5 (1.73 g, 2.83 mmol) in dry THF (50 ml). The mixture was stirred at 65° C. for 3 hours under $N_2$. The reaction was cautiously quenched with water (5 ml), followed by filtration of solids. Evaporation of the filtrate and flash chromatography on silica gel, eluting with 5% concentration $NH_4OH$ in methanol, produced 0.6 g (44%) of 5 as an oil: NMR δ1.09 (m, 6 H), 1.47 (m, 8 H), 2.64 (m, 16 H), 3.59 (m, 4 H), 3.75 (m, 2 H), 7.28 (m, 10 H). Anal. calcd. for $C_{30}H_{50}N_4O_2$: C 72.25, H 10.10, N 11.23. Found: C 72.31, H 10.07, N 11.15.

EXAMPLE 6

$N^1,N^{14}$-Diethyl-3 (R), 12(R)-dihydroxyhomospermine tetrahydrochloride [$(HO)_2$DEHSPM](7).

Pd on C (10%, 0.4 g) was added to a solution of 6 (2.26 g, 4.53 mmol) in concentrated HCl (3 ml) and EtOH (100 ml) and the suspension was degassed three times with $N_2$. After stirring under hydrogen (1 atm, 3 hours), the catalyst was filtered off and washed with water (10 ml). The solvents were removed under reduced pressure to give a white solid. Recrystallization from aqueous EtOH gave 1.5 g (72%) of 7 as a crystalline solid: NMR $(D_2O)$ δ1.07 (t, 6 H, J =2.4), 1.60 (m, 4 H), 1.74 (m, 4 H), 2.91 (m, 16 H), 3.84 (m, 2 H). Anal. calcd. for $C_{16}H_{42}Cl_4N_4O_2$: C 41.39, H 9.12, N 12.07. Found: C 41.51, H 9.06, N 12.00.

EXAMPLE 7

3(R), 12(R)-Dihydroxyhomosperminetetrahydrochloride [$(HO)_2$HSPM] (8).

HCl (1 N, 10 ml) and 10% Pd/C (0.08 g) were added to a solution of 4 (0.764 g, 1.73 mmol) in methanol (100 ml) and the suspension was flushed three times with nitrogen. The mixture was exposed to hydrogen for 3 hours at atmospheric pressure followed by filtration of catalyst on Celite. The filtrate was evaporated in vacuum to give a white solid which was recrystallized from aqueous ethanol to produce 0.56 g (80%) of 8 as a crystalline solid: NMR $(D_2O)$ δ1.63 (m, 8 H), 2.97 (m, 12 H), 3.92 (m, 2 H). Anal. calcd. for $C_{12}H_{34}Cl_4N_4O_2$: C 35.31, H 8.39, N 13.72. Found: C 35.60, H 8.22, N 13.60.

The following examples demonstrate the effectiveness and low toxicity of the hydroxy polyamines of the invention for resecting the exocrine portion of the pancreas.

I. Effect of $(OH)_2$DEHSPM on Pancreatic Cells in vitro $(OH)_2$DEHSPM was tested in a series of $IC_{50}$ assays in the human pancreatic cell carcinoma line PANC-1 (doubling time 36 hr.). The results are set forth in Table 1 below.

TABLE 1

| Time point (hr.) | $IC_{50}$ ($\mu m$) |
| --- | --- |
| 96 | >100 |
| 144 | 0.50 |
| 240 | 0.12 |

(OH)$_2$DEHSPM was also tested in the acinar-derived cell line AR42J. The results of a series of IC$_{50}$ assays are shown in Table 2 below:

TABLE 2

Effect of (R,R) - (HO)$_2$DEHSPM on the Growth of AR42J Cells

| Treatment Period (days) | IC$_{50}$ ($\mu$m) |
|---|---|
| 4 (=1.33 doublings) | 90 |
| 6 (=2 doublings) | 1.2 |
| 12 (=4 doublings*) | 0.09 |

*This number of doublings is the same as in 48 hours in L1210 cells.

In addition, the effect of (OH)$_2$DEHSPM on the native polyamine levels in this cell line was evaluated. The results are set forth in Table 3 below:

TABLE 3

Polyamine Pool Analysis For (R,R)—(HO)$_2$DEHSPM

| Polyamine | PUT[a] | SPD[a] | SPM[a] | Analogue[b] |
|---|---|---|---|---|
| R,R—(HO)$_2$DEHSPM 5 $\mu$m | 0 | 21 | 82 | 4748 |

[a]Native polyamine levels in analogue-treated cells expressed as % polyamine pools relative to untreated controls.
[b]Analogue level expressed as pmol/million cells.

II. (HO)$_2$DEHSPM in vivo (Mice)

Male BDF mice (12 weeks old, weight approximately 28.9 g) were implanted with the pancreatic ductal cell carcinoma #03 3 days before beginning treatment with (HO)$_2$DEHSPM. In one group, treatment started at 50 mg/kg/injection IV 4 times daily (QD) on days 3 and 4; the weight loss on day 5 resulted in cessation of treatment. Treatment was restarted at 20 mg/kg/injection QD on days 14, 17 and 18, a total dose of 240 mg/kg over 15 days. A 38% weight loss was noted (Table 4), although none of the mice died. There was only some reduction in tumor burden, to 64% of control. Non-tumor-bearing mice subjected to this same regimen exhibited a 30% body weight loss by day 35. An IV treatment regimen of 25 mg/kg/injection QD for 3 days followed by 10 mg/kg/injection for the remaining 12 days for a total dose of 205 mg/kg, however, resulted in a significant lowering of tumor burden, to 17% of controls (Table 4), and the weight loss observed was somewhat less dramatic as well (Table 4). Decreasing the previous dosing regimen by half, to a total of 102.5 mg/kg over 15 days, resulted in no significant weight loss; however, there was little decrease in tumor burden (Table 4).

TABLE 4

Evaluation of (HO)$_2$DEHSPM Against Early Stage Pancreatic Ductal Adenocarcinoma #03

| Cage | Treatment | Drug Route | Schedule | Total Dosage (mg/kg) | Mean Body Wt. Loss (g/mouse) | Percent Body Wt. Loss | Day of Wt. Loss Nadir | Drug Deaths (days of death) |
|---|---|---|---|---|---|---|---|---|
| 1 | No Rx | — | — | — | +5.0 | +17.0 | 24 | — |
| 2 | DEHSPM | IV | QD 3, 4, 6–9, 14, 17, 18 | 240 | −11.2 | −38.0 | 35 | 0/5 |
| 3 | DEHSPM (NTB) | IV | QD 3, 4, 6–9, 14, 17, 18 | 240 | −8.5 | −30.0 | 35 | 0/2 |
| 4 | DEHSPM | IV | QD 3–18 | 205 | −8.6 | −29.0 | 35 | 0/5 |
| 5 | DEHSPM (NTB) | IV | QD 3–18 | 205 | −7.5 | −26.0 | 35 | 0/2 |
| 6 | DEHSPM | IV | QD 3–18 | 102.5 | −0.4 | — | 7 | 0/5 |
| 7 | DEHSPM (NTB) | IV | QD 3–18 | 102.5 | −1.0 | −3.0 | 23 | 0/2 |

| Cage | Median Tumor Burden (mg) on day 18 (range) | T/C % | Tumor Free on Day | Time to 1000 mg days (range) | T-C (days) | Log Kill | Comments |
|---|---|---|---|---|---|---|---|
| 1 | 1020 (180–1783) | — | 0/6 | 17.8 (14.75–24.5) | — | — | — |
| 2 | 651 (138–1324) | 64 | 0/5 | — | — | — | Inactive |
| 3 | — | — | — | — | — | — | — |
| 4 | 172 (63–965) | 17 | 0/5 | 26.8 (18–28) | 9 | 0.8 | — |
| 5 | — | — | — | — | — | — | — |
| 6 | 617 (270–748) | 60 | 0/5 | — | — | — | Inactive |
| 7 | — | — | — | — | — | — | — |

Mice: BDF Males, DOB: 11/04/96; Avg. Wts.: 28.9 g/mouse.
Tumor: P03/170, Implanted 02/07/97
Td = 3.5 days
NTB = Non-tumor-bearing toxicity controls
(HO)$_2$DEHSPM was provided as a white powder; when dissolved in H$_2$O, the solution had a pH of 5. Total volume in each injection was 0.2 ml/mouse.

III. (HO)$_2$DEHSPM in vivo (Beagles)
Part A: Initial (R,R)-(HO)$_2$DEHSPM Results

BACKGROUND

Five male beagles approximately 6–8 months of age were obtained from Harlan Sprague Dawley. They were provided with food and water ad libitum and were allowed to acclimate to their new surroundings for two weeks. The animals were weighed prior to starting drug administration and were weighed once per week during the drug dosing period. A CBC and chemistry panel were performed every 1–2 weeks. The drug study was performed in two stages. In the first phase, three animals were given the drug at 2.15 mg/kg/day (dogs #516, 518 and 526). In the second phase, the other two dogs were given the drug at 4.3 mg/kg/day (dogs #490 and 494). In both experiments, the daily drug dose was divided and administered twice daily at 12-hour intervals.

The results of the long-term washout and subsequent toxicity of the (R,R)-(HO)$_2$DEHSPM are summarized. Briefly, the drug was initially thought to be well tolerated at the 2.15 mg/kg/day dose. In order to compare the long-term washout of the (HO)$_2$DEHSPM as compared to DEHSPM, it was decided not to sacrifice the animal (#516) until 75-days post-drug. Approximately two months post-drug, it was noted that the dog had begun losing weight. A routine chemistry panel showed an elevated SGPT and a fecal check revealed a large amount of fat in the dog's stool. Chronic pancreatitis or intestinal malabsorption was suspected. A serum trypsin-like immunoreactivity test was conducted which confirmed the presence of exocrine pancreatic insufficiency. Inasmuch as the dog was imminently scheduled for sacrifice, no treatment was initiated. At necropsy 75-days post-drug, there was little, if any, abdominal fat and the animal's pancreas was atrophied as described below.

The exocrine pancreatic insufficiency that was observed in this animal was not immediately attributed to the drug, as the animals that had been given the (HO)$_2$DEHSPM at 4.3 mg/kg/day, and who were at that time 41- and 46-days postdrug, were not showing any signs of malabsorption/maldigestion. However, approximately 55–60 days post-drug, it was noted that although the dogs in the 4.3 mg/kg/day group (#490 and 494) were eating well and were bright, alert and responsive, they began losing weight (2 kg). Blood chemistries revealed an elevated SGPT; additional tests including qualitative fecal fat and trypsin-like immunoreactivity were conducted and confirmed the presence of exocrine pancreatic insufficiency. In order to further confirm the exocrine pancreatic insufficiency, additional experiments were performed.

PROTOCOL

The two dogs (#490 and 494) were fed a prescription canned and dry dog food and were supplemented with Viokase, a pancreatic enzyme preparation, by mixing three tablets with food or by oral administration immediately before each feeding. The dogs were maintained on this regimen for approximately three weeks. During this time, their weight and blood chemistries were closely monitored. The Viokase supplementation was then stopped and the same parameters were again evaluated. One week after the Viokase administration had ceased, the animals were euthanized and tissues were taken for histology and for the determination of tissue polyamine levels.

RESULTS

Although the dogs' weight fluctuated from day-to-day, there was a definite increase in body weight during the time that the Viokase was being administered. For example, dog #490 has a starting body weight of 9.1 kg and an ending body weight, the day that the Viokase treatment was stopped (day #23), of 10.2 kg, a gain of 1.1 kg. Likewise, dog #494 has a starting body weight of 10.4 kg and an ending body weight of 11.6 kg, a gain of 1.2 kg. However, once the Viokase administration ceased, both dogs quickly lost all of the weight that they had gained. When they were sacrificed one week post-Viokase, dog #490 weighed 9.0 kg and dog #494 weighed 10.6 kg, a loss of 1.2 and 1.0 kg, respectively. The weight gain with Viokase supplementation and subsequent weight loss once the Viokase ceased provided further evidence of the suspected exocrine pancreatic insufficiency.

In addition to monitoring the dogs' body weight, additional blood chemistry parameters were also evaluated. When blood was drawn from the dogs approximately 60-days post-drug, their liver function tests (alkaline phosphatase and SGPT) were significantly increased as compared to the normal canine range. For example, dog #490 had an alkaline phosphatase of 542 U/L and an SGPT of 1108 U/L, while dog #494 had an alkaline phosphatase of 436 U/L and an SGPT of 776 U/L (normal alkaline phosphatase is 37–105 U/L, while the normal SGPT is 0–40 U/L). Inasmuch as veterinary clinical pathology textbooks suggest that an increase in liver enzymes could be secondary to a pancreatic problem, the animals' liver function as related to the administration of Viokase was evaluated. The liver function values of both animals quickly returned to normal once Viokase administration was begun and these values did not change significantly during the seven days that the dogs were off of the Viokase.

In addition to the above tests, a series of trypsin-like immunoreactivity (TLI) tests were also performed. The normal canine range for the TLI is 5–35 ng/ml and values below 2.0 ng/ml are diagnostic for exocrine pancreatic insufficiency. The TLI results for both of the dogs were less than 2.0 ng/ml and remained abnormally low throughout the Viokase and post-Viokase administration periods. It is of interest to note that although the exocrine pancreas was clearly compromised, the endocrine functionality was not; the glucose levels were normal throughout the experiment. Finally, the dogs were sacrificed one week after the Viokase administration ceased. At necropsy, there was little, if any, abdominal fat and the pancreases of both animals were severely atrophied, and the pancreas of dog #490 could not be located.

75-, 78-, 88- and 92-days post-treatment—Severe atrophy of the pancreas was observed at necropsy in all cases. In the worst case, it was difficult to recognize the remnants of the pancreas as such since the vast portion of the organ had atrophied. For example, in one case (75-days post-treatment), two samples were collected just to ensure that pancreatic tissue had been obtained. One was confirmed histopathologically to be of pancreatic origin with moderate to severe pancreatitis and polyamine analysis revealed a polyamine profile similar to other unambiguously identified tissue of pancreatic origin; the second sample turned out to be a piece of mesenteric fat. In this 75-day post-treatment sample with severe atrophy, the drug had been almost completely washed out, as was the case for the 88- and 92-day post-treatment samples. In all four samples (75-, 78-, 88- and 92-days post-treatment), the native polyamine levels had stabilized, but at a much lower level than the control pancreas.

This may represent the basal polyamine level of the endocrine (Islets) pancreas since the exocrine pancreas had largely disappeared from these tissues.

Part B: A Comparison of (R.R)- v. (S,S)-(HO)₂DEHSPM

As the pancreatic insufficiency side-effect that was observed after the administration of the (R,R)-(HO)₂DEHSPM to the beagles may have been related to the (R,R)-chirality of the molecule, the (S,S)-enantiomer was synthesized and was compared in a head-to-head fashion with the (R,R)-enantiomer. To perform this experiment, five male beagles approximately 6–8 months of age were obtained from Harlan Sprague Dawley. There were provided with food and water ad libitum and were allowed to acclimate to their new surroundings for two weeks. The animals were weighed prior to starting drug administration and were weighed once per week during the drug dosing period. A CBC and chemistry panel and a Holter monitor were performed once per week. In addition to the usual tests, additional pancreatic function-specific tests were also performed. These additional evaluations included a fecal trypsin test, examination of the feces for fecal fat and serum trypsin-like immunoreactivity determinations. It was hoped that these signs of pancreatic insufficiency would only appear in the animals given the (R,R)-enantiomer and would not be observed in the dogs that were given the (S,S)-molecule. The pancreatic insufficiency may not become evident until approximately 7–8 weeks post-drug. At the conclusion of the experiment, all of the animals were sacrificed and the histology and tissue polyamine levels were determined.

PROTOCOL

Five male beagles approximately 6–8 months of age were obtained from Harlan Sprague Dawley. They were provided with food and water ad libitum and were allowed to acclimate to their new surroundings for two weeks. Once two sets of baseline data were obtained, the animals were randomly divided into three groups: two of the dogs (#468 and 500) received the (R,R)-(HO)₂DEHSPM; two of the animals (#440 and 476) were given (S,S)-(HO)₂DEHSPM; and one dog (#452) served as an untreated (saline only) control. The dogs were given the (R,R)- or (S,S)-(HO)₂DEHSPM at a dose of 4.3 mg/kg/day subcutaneously in divided doses, 2.15 mg/kg BID. Although it had been planned to give the drug for two weeks, due to the development of bloody diarrhea and anorexia in one of the (R,R)-treated dogs (#468), the study was stopped on day #13.

The animals were weighed weekly during the acclimation period, the drug dosing period and throughout the post-drug observational period. A CBC, chemistry panel and pancreatic function tests (trypsin-like immunoreactivity, fecal trypsin, fecal fat, etc.) were performed once per week. Additional tests, e.g., glucose tolerance and fat absorption, were performed as necessary. The dogs were Holter monitored twice during the acclimation period and then weekly during drug dosing.

| Results | |
| --- | --- |
| Drug: | Control - saline only |
| Dose: | 0.5 cc/kg twice daily |
| Route: | subcutaneously |
| Dog #: | 452 |

| -continued | |
| --- | --- |
| Results | |
| Initial weight: | 12.2 kg |
| Final experimental weight: | 12.1 kg |
| Weight at sacrifice: | 12.8 kg |

1. Dog #452 was given saline subcutaneously twice daily for 13 days.
2. He was fed Purina Dog Chow ad libitum and was given free access to water.
3. At the start of the experiment, the animal weighed 12.2 kg. At the end of the saline dosing period, the animal weighed 12.1 kg, a loss of 0.1 kg. The animal continued to gain about 1.0 kg per week during the recovery period and had a final body weight of 12.8 kg.
4. The dog was bright, alert and responsive at the start of the study and remained so throughout the "dosing" period. He ate well and had normal urine and feces production.
5. At necropsy 64-days "post-drug," the dog's pancreas appeared well-defined, about 12–15 cm long and about 30 grams in weight. The native polyamine content of this tissue is 4–5 times higher than that of any other tissue analyzed.

Drug: (R,R)-(HO)₂DEHSPM
Dose: 4.3 mg/kg/day (2.15 mg/kg every 12 hours) for 13 days
Route: subcutaneously 1. Dogs #468 and 500 were given (R,R)-(HO)₂DEHSPM subcutaneously twice daily for 13 days.
2. They were fed Purina Dog Chow ad libitum and given free access to water.
3. Polyamine levels in the pancreas were also analyzed at several time points post-drug.
4. At the start of the experiment, dog #468 weighed 14.4 kg and dog #500 weighed 12.8 kg. The latter animal's weight never exceeded 13.2 kg. At the end of the drug dosing period, dog #468 weighed 13.0 kg, a loss of 1.4 kg; dog #500 weighed 13.2 kg, a gain of 0.4 kg.
5. The pancreatic tissue samples presented with no histological abnormalities at 10-days post-drug. Interestingly, the pancreatic concentration of drug (parent+metabolite) exceeded 1,000 $\mu$m, more than twice the level in any other tissue examined (liver concentration=500 $\mu$m). The pancreatic native polyamine pools (most especially SPD) were markedly diminished compared to untreated control tissue:

[SPM]$_{control}$=3,985 $\mu$m v. [SPM]$_{10}$-days post-treatment= 2,548 $\mu$m (64% of control)

[SPD]$_{control}$=2,820 $\mu$m v [SPD]$_{10}$-days post-treatment =721 $\mu$m (25.6% of control)

6. Dog #468 was bright, alert and responsive until day thirteen of drug administration. At that time, he developed bloody diarrhea and stopped eating. The dog was fed boiled chicken and rice, as well as Nutrical (a caloric supplement) and cat food and was slowly weaned back to regular dog food. Frank and/or occult blood was found in the dog's stool until about 17-days post-drug.
7. Dog #500 was bright, alert and responsive throughout the experiment. He developed bloody diarrhea one-day post-drug. However, stool consistency had normalized by one week post-drug.
8. Approximately five weeks post-drug, both dogs began losing weight very rapidly. Their TLI began to decrease and fecal trypsin test results were abnormal. In addition, when the animals were fed a fatty meal, the postfeeding serum samples were clear, indicating an inability to digest fats. The inability to digest fats was confirmed when this test was repeated and the fatty meal was supplemented with Viokase (a pancreatic enzyme supplement). In the latter experiment, the post-feeding serum samples were lipemic, a normal response. Taken together, these results confirmed a diagnosis of exocrine pancreatic insufficiency. Interestingly, when a glucose tolerance test was performed, the animals displayed a "normal" response, thus indicating that the endocrine pancreas was functional. (Although dog #468's blood glucose level exceeded 160 mg/dl due to his deteriorated condition and because his blood glucose levels returned to normal during the 3.5 hours of the experiment, his response was considered normal.) Finally, the alopecia that was observed with the animals in the earlier (R,R)-(HO)$_2$ DEHSPM studies was also noted in these animals. The dogs continued to deteriorate; dog #468 was euthanized 52-days post-drug and dog #500 was euthanized 58-days post-drug.

9. At necropsy, the dogs' pancreases were readily discernible, but greatly atrophied (about one-fourth the control weight) and flattened in appearance. Histopathology showed moderate to severe atrophy of the exocrine pancreases, including marked degranulation of the Acinar cells.

10. The total drug concentration (parent+metabolite) remained virtually unchanged from that present at 10-days post-treatment, but native polyamines were at this time point severely depleted compared to untreated control:
[SPM]$_{52}$-days post-treatment=860 $\mu$m (21.6% of control)
[SPD]$_{52}$-days post-treatment=156 $\mu$m (5.5% of control)
Drug: (S,S)-(HO)$_2$DEHSPM
Dose: 4.30 mg/kg/day (2.15 mg/kg every 12 hours) for 13 days
Route: subcutaneously 1. Dogs #440 and 476 were given (S,S)-(HO)$_2$DEHSPM subcutaneously twice daily for 13 days.
2. They were fed Purina Dog Chow ad libitum and given free access to water.
3. At the start of the experiment, dog #440 weighed 11.8 kg. At the end of the drug dosing period, the animal weighed 11.4 kg, a loss of 0.4 kg. The dog's weight peaked at 12.4 kg four weeks post-drug. At sacrifice, the dog weighed 11.0 kg. Dog #476 weighed 14.0 kg at the start of the experiment. At the end of the drug dosing period, the animal weighed 13.8 kg, a loss of 0.2 kg. The dog's weight peaked four weeks post-drug at 14.8 kg; at sacrifice, the animal weighed 12.3 kg.
4. Dog #440 was bright, alert and responsive throughout the experiment. He developed bloody diarrhea one-day post-drug. However, stool consistency had normalized by one week post-drug.
5. Approximately five weeks post-drug, dogs #440 and 476 began losing weight very rapidly. The TLI began to decrease and fecal trypsin test results were abnormal. In addition, when the animals were fed a fatty meal, the post-feeding serum samples were clear, indicating an inability to digest fats. This was confirmed when the tests was repeated and the fatty meal was supplemented with Viokase. In this case, the post-feeding serum samples were lipemic, a normal response. These results confirmed the diagnosis of exocrine pancreatic insufficiency. However, when a glucose tolerance test was performed, the animals displayed a normal response, thus indicating that the endocrine pancreas was functional in both animals. Interestingly, the alopecia that was observed with the animals in the earlier studies was also noted in these animals. The dogs continued to deteriorate; dog #440 was euthanized 58-days post-drug and dog #476 was euthanized 64-days post-drug.
6. At necropsy, the dogs' pancreases were indistinguishable histologically with moderate to severe atrophy of the exocrine pancreases.

7. Pancreatic polyamine levels were severally evaluated post-drug and compared to those observed with (R,R)-(OH)$_2$ DEHSPM. A substantial amount of drug was present in each sample:
[Drug]$_{(parent+metabolite)}$=620±25 $\mu$m
Native polyamine levels were almost identical to the corresponding (R,R)-(HO)$_2$DEHSPM treated tissues:
PUT=15±8; SPD=105±17; and SPM=530±22.

Two animals were also treated with DEHSPM at a dose equimolar to the (HO)$_2$DEHSPM dosage and sacrificed at 1- and 75-days after the final treatment. A substantial amount of drug is accumulated by the pancreas, amounts comparable to that seen with (HO)$_2$DEHSPM. At 1-day post-treatment, the total amount of drug:
(parent+metabolites)$_1$-day post-treatment=951 $\mu$m.
Moreover, the initial effect on native polyamine contents is roughly comparable for DEHSPM and (HO)$_2$DEHSPM:
[SPM]$_{1\text{-}day\ post\text{-}treatment}$=2,770 $\mu$m (69.5% of control)
[SPD]$_{1\text{-}day\ post\text{-}treatment}$=863 $\mu$m (30.6% of control).
At 75-days post-treatment, a substantial amount of DEHSPM remains in the pancreas:
(parent+metabolites)$_{75\text{-}days\ post\text{-}treatment}$=595 $\mu$m.
However, in remarkable contrast to the (HO)$_2$DEHSPM-treated tissues, the native polyamine levels in the DEHSPM-treated pancreases have substantially recovered to more nearly normal levels:
PUT=60 $\mu$m; SPD=1,572 $\mu$m (55.7% of control); and SPM=3,162 $\mu$m (79.3% of control).

The nearly normal polyamine pools are mirrored by the anatomy. The pancreas is essentially normal macroscopically and microscopically with well-defined Acinar cells with intensely eosinophilic zymogen granules and ducts lined with tall columnar epithelium and well-defined Islets. Exocrine and endocrine pancreatic functions appeared normal.

It will thus be understood that all of the possible diastereoisomers of the hydroxy polyamines of the above structural formula should be effective active agents in the compositions and methods of the invention. Accordingly, as utilized when describing the present invention, the above structural formula includes all of the diastereoisomers, as well as racemates, of the hydroxy polyamines embraced thereby.

For the utility mentioned herein, the amount required of active agent, the frequency and the mode of its administration will vary with the identity of the agent concerned and with the nature and severity of the condition being treated and is, of course, ultimately at the discretion of the responsible physician or veterinarian. In general, however, a suitable dose of agent for all of the above-described conditions will lie in the range of about 0.01 mg/kg to about 30 mg/kg, and preferably about 0.5 mg/kg to about 10 mg/kg, of mammal body weight being treated. The composition is preferably administered parenterally (intravenously, intradermally, intraperitoneally, intramuscularly or subcutaneously), but may also be administered orally for a period of time sufficient to result in the resection of the exocrine portion of the pancreas. The precise period of time will depend in each case, of course, upon the animal under treatment and the dosage employed. By monitoring the pancreatic exocrine function of the animal according to conventional methods during administration of the hydroxy polyamines, the time of treatment required can be accurately gauged.

While it is possible for the agents to be administered as the raw substances, it is preferable to present them as a pharmaceutical formulation. The formulations of the present invention, both for veterinary and human use, comprise the agents together with one or more pharmaceutically acceptable carriers therefor and optionally other therapeutic ingredients. The carrier(s) must be "acceptable" in the sense of being compatible with the other ingredients of the formulation and not deleterious to the recipient thereof. Desirably, the formulations should not include oxidizing agents and other substances with which the agents are known to be incompatible. The formulations may conveniently be presented in unit dosage form and may be prepared by any of the methods well known in the art of pharmacy. All methods include the step of bringing into association the agent with the carrier which constitutes one or more accessory ingredients. In general, the formulations are prepared by uniformly and intimately bringing into association the agent with the carrier(s) and then, if necessary, dividing the product into unit dosages thereof.

Formulations suitable for oral administration may be in the form of discrete units such as capsules, cachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

A tablet may be made by compressing or molding the active ingredient optionally with one or more accessory ingredients. Compressed tablets may be prepared by compressing, in a suitable machine, the active ingredient in a free-flowing form such as a powder or granules, optionally mixed with a binder, lubricant, inert diluent, surface active agent or dispensing agent. Molded tablets may be made by molding, in a suitable machine, a mixture of the powdered active ingredient and a suitable carrier moistened with an inert liquid diluent.

Formulations suitable for parenteral administration conveniently comprise sterile aqueous preparations of the agents which are preferably isotonic with the blood of the recipient. Suitable such carrier solutions include phosphate buffered saline, saline, water, lactated ringers or dextrose (5% in water). Such formulations may be conveniently prepared by admixing the agent with water to produce a solution or suspension which is filled into a sterile container and sealed against bacterial contamination. Preferably, sterile materials are used under aseptic manufacturing conditions to avoid the need for terminal sterilization.

Formulations for oral or parenteral administration may optionally contain one or more additional ingredients among which may be mentioned preservatives such as methyl hydroxybenzoate, chlorocresol, metacresol, phenol and benzalkonium chloride. Such materials are of special value when the formulations are presented in multi-dose containers.

Buffers may also be included to provide a suitable pH value for the formulation and suitable materials include sodium phosphate and acetate. Sodium chloride or other appropriate salts may be used to render a formulation isotonic with the blood. If desired, the formulation may be filled into the containers under an inert atmosphere such as nitrogen or may contain an anti-oxidant and are conveniently presented in unit dose or multi-dose form, for example, in a sealed ampoule.

It will be appreciated that while the agents described herein form acid addition salts and carboxylic acid salts, the biological activity thereof will reside in the agent itself. These salts may be used in human and in veterinary medicine and presented as pharmaceutical formulations in the manner and in the amounts (calculated as the base) described hereinabove, and it is then preferable that the acid moiety be pharmacologically and pharmaceutically acceptable to the recipient. Examples of such suitable acids include (a) mineral acids: hydrochloric, hydrobromic, phosphoric, metaphosphoric and sulfuric acids; (b) organic acids: tartaric, acetic, citric, malic, lactic, fumaric, benzoic, glycollic, gluconic, gulonic, succinic and aryl-sulfonic, for example, p-toluenesulfonic and methanesulfonic acids.

The active agent or pharmaceutically acceptable derivatives or salts thereof may also be mixed with other pharmaceutically active materials that do not interfere with the desired action or with materials that enhance or supplement the desired action. Examples of appropriate other agents include antibiotics, anti-fungals, anti-virals, antihistamines, immunosuppressants and other anti-inflammatory or analgesic compounds the like.

I claim:

1. A method of chemically resecting the exocrine portion the pancreas of a human or non-human mammal in need thereof comprising administering to said mammal an amount of a hydroxy polyamine or a salt thereof with a pharmaceutically acceptable acid sufficient to resect the exocrine portion of the pancreas thereof, but insufficient to substantially alter the endocrine portion thereof, said hydroxy polyamine having a structure according to the formula:

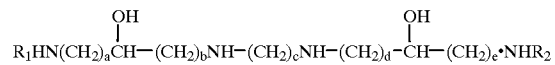

wherein: $R_1$ and $R_2$ may be the same or different and are alkyl having 1 to 6 carbon atoms or aryl or aralkyl having up to 12 carbon atoms;

a, b, d and e may be the same or different and are integers from 1 to 4; and c is an integer from 2 to 6.

2. A method according to claim 1, wherein said hydroxy polyamine has the formula:

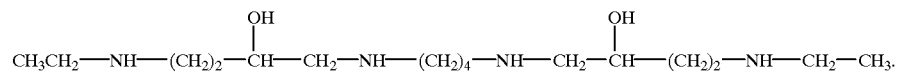

* * * * *